(12) United States Patent
Endriss

(10) Patent No.: US 11,485,600 B2
(45) Date of Patent: Nov. 1, 2022

(54) ROLLING DEVICE

(71) Applicant: Ditte Endriss, Ulm (DE)

(72) Inventor: Ditte Endriss, Ulm (DE)

( * ) Notice: Subject to any disclaimer, the term of this patent is extended or adjusted under 35 U.S.C. 154(b) by 416 days.

(21) Appl. No.: 16/786,395

(22) Filed: Feb. 10, 2020

(65) Prior Publication Data
US 2020/0172364 A1 Jun. 4, 2020

Related U.S. Application Data

(63) Continuation of application No. PCT/EP2018/071460, filed on Aug. 8, 2018.

(30) Foreign Application Priority Data

Aug. 8, 2017 (DE) .................... 10 2017 118 007.9

(51) Int. Cl.
| | |
|---|---|
| *B65H 35/00* | (2006.01) |
| *B65H 16/00* | (2006.01) |
| *A61F 15/00* | (2006.01) |
| *A61F 15/02* | (2006.01) |

(52) U.S. Cl.
CPC ......... *B65H 35/008* (2013.01); *A61F 15/002* (2013.01); *A61F 15/02* (2013.01); *B65H 16/005* (2013.01); *B65H 2301/51532* (2013.01); *B65H 2402/43* (2013.01)

(58) Field of Classification Search
CPC ........................... B65H 35/008; B65H 16/005; B65H 2402/43; B65H 2301/51532; B65H 35/0073; B65H 35/0013; A61F 15/002; B25H 35/0006

USPC ...... 242/588; 225/51, 52, 56, 11–13, 57–66, 225/68, 84–89, 24, 34, 77; 156/577, 523, 156/574, 554, 516, 576
See application file for complete search history.

(56) References Cited

U.S. PATENT DOCUMENTS

| | | | | |
|---|---|---|---|---|
| 2,614,579 | A * | 10/1952 | Crockett ................. | F16K 31/26 137/444 |
| 2,947,204 | A * | 8/1960 | Pine ..................... | B25H 1/0035 408/124 |
| 2,989,025 | A * | 6/1961 | Chaffee .............. | B65H 35/0046 225/56 |

(Continued)

FOREIGN PATENT DOCUMENTS

| | | |
|---|---|---|
| CN | 203229251 U | 10/2013 |
| DE | 27 58 563 | 7/1979 |

(Continued)

*Primary Examiner* — Ghassem Alie
(74) *Attorney, Agent, or Firm* — Muncy, Geissler, Olds & Lowe, P.C.

(57) ABSTRACT

A device for dispensing adhesive tape or for dispensing medical products stored on a roll, that includes a base plate, fitted with a pin upon which a roll or adhesive tape is attached, and a tearing section with a tearing blade spaced at a distance from the pin. The base plate is associated with a fastening section for partially gripping a rod or a bar. The fastening section includes an arm connected to the base plate and that merges with a crosspiece. The crosspiece is fixed to a free arm such that the rod or the bar can be accommodated between the free arm and the connected arm. Also included is at least one fastening unit that is provided to join the connected arm to the free arm.

18 Claims, 2 Drawing Sheets

(56) References Cited

U.S. PATENT DOCUMENTS

| | | | | |
|---|---|---|---|---|
| 3,260,432 | A | * | 7/1966 | Smith .................. B65B 25/145 225/77 |
| 4,606,485 | A | * | 8/1986 | Rankin .............. B65H 35/0006 225/82 |
| 5,392,676 | A | | 2/1995 | Drury |
| 5,445,703 | A | * | 8/1995 | Steeves ................ B65H 35/004 156/577 |
| 9,586,782 | B2 | * | 3/2017 | Chalifoux ............ B65H 35/002 |
| 2015/0000452 | A1 | * | 1/2015 | Hirotomi ............... B62K 23/02 74/488 |
| 2015/0090849 | A1 | | 4/2015 | Breitweiser et al. |
| 2016/0001999 | A1 | * | 1/2016 | Gallegos ............ B65H 35/0026 225/80 |

FOREIGN PATENT DOCUMENTS

| | | | | |
|---|---|---|---|---|
| DE | 197 31 428 A1 | | 1/1999 | |
| DE | 10 2004 018 618 A1 | | 7/2005 | |
| DE | 20 2013 007 461 U1 | | 12/2013 | |
| DE | 20 2014 103 429 U1 | | 12/2015 | |
| DE | 202016101959 U1 | * | 6/2016 | ............. E01F 13/02 |
| EP | 0 963 933 A1 | | 12/1999 | |
| GB | 0822101 A1 | * | 3/1998 | ............. B44C 7/025 |
| JP | S 63-3052 U | | 1/1988 | |

\* cited by examiner

ROLLING DEVICE

This nonprovisional application is a continuation of International Application No. PCT/EP2018/071460, which was filed on Aug. 8, 2018, and which claims priority to German Patent Application No. 10 2017 118 007.9, which was filed in Germany on Aug. 8, 2017, and which are both herein incorporated by reference.

BACKGROUND OF THE INVENTION

Field of the Invention

The present invention relates to a device for dispensing adhesive tape or for dispensing medical products stored on a roll, comprising a base plate, fitted with a pin for receiving the roll or the adhesive tape, further a tearing section with a tearing blade spaced at a distance from the pin, wherein a fastening section is connected to the base plate for at least partially encompassing a rod, a bar or the like.

Description of the Background Art

One such dispenser is disclosed in DE 20 2014 103 429 U1. One disadvantage of using this dispensing device for rolls of medical products such as plasters, gauze bandages, bandaging material etc. is that the risk of infection increases due to handling. To detach a medical product from the dispensing device, one hand must always touch the dispensing device and the other hand must always touch the tape or medical product. In this way, bacteria, viruses and multi-resistant pathogens are transferred from the hand to the dispensing device. Consequently, pathogens may be unintentionally transferred to patients with every use.

Further disadvantageous dispensing devices known from the prior art are disclosed in German patent application DE 10 2004 018 618 A1 and DE 197 31 428 A1.

European patent application EP 0 963 933 A1 also discloses a dispensing device.

SUMMARY OF THE INVENTION

It is therefore an object of the present invention to develop the aforementioned type of dispensing device in such a way as to enable a more hygienic and safe handling.

In an exemplary embodiment, the fastening section comprises an arm connected to the base plate merging with a crosspiece, which is fixed to a free arm such that the rod, bar or the like can be accommodated between the free arm and the connected arm, at least one fastening unit being provided to join the connected arm to the free arm. The corresponding design of the fastening section for at least partially encompassing a rod, a bar or the like enables single-handed operation, wherein it fixes the dispensing device in an operationally safe manner to the rod, the bar or the like. The dispensing device is preferably mounted on an IV pole, a bed, a baseboard or the like—for instance by hinging/hanging. Solely the strip, which has been detached from the roll, comes into contact with the hand. The transfer of bacteria or germs to the dispensing device or to the roll, i.e., the adhesive tape roll, is thus considerably reduced. A medical product stored on a roll may include plasters, gauze bandages or any other bandaging material. In one preferred embodiment, the tearing blade is fitted with teeth.

To ensure that the dispenser attains angular stability, it has proved advantageous to provide two fastening units, which join the free arm with the connected arm at the respective edges.

Secure fixation is also achieved by ensuring that the at least one fastening unit joins the free arm with the connected arm in such a way as to create a space by means of the free arm, the crosspiece and the connected arm to accommodate or allow passage of the rod, which is bounded by the at least one fastening unit.

For quick and easy mounting of the dispensing device, a provision is made, in particular, for the fastening section to be formed as a clamping element to clamp the rod, bar or the like, so as to ensure in particular that the at least one fastening unit joins the free arm to the connected arm in such a way as to clamp a rod, bar or the like accommodated in the fastening section.

In order to facilitate the handling of the dispenser, it is in particular provided that the fastening section is preferably shaped as a curve or a groove. In this case, the free arm may be positioned either parallel or concave to the base plate.

In order to mount the dispensing device on rods, bars or the like of varying diameter or width, it is advantageous for the free arm and the arm connected to the base plate to be designed to accommodate an adapter between them to adjust an inner circumference of the fastening section. In this case, in particular, it is preferred for the outside diameter of the adapter to correspond approximately to the inside diameter of the fastening section. Alternatively, or in addition, the adapter can also be formed from an alternate material to the fastening section. For instance, the adapter may be formed from an elastic material to protect the rod from scratches and the like or may have an anti-slip coating to ensure that the dispensing device adheres to the rod, a bar or the like. Here, the shape of the adapter is aligned with the shape of the fastening section: If the fastening section is formed as an arc, the adapter is also formed as an arc. In this case, the adapter is preferably designed in such a way as to ensure that the length of the fastening section corresponds to a length of the adapter, i.e. the adapter extends completely over the length of the fastening section. In an alternative embodiment, it is possible to design the adapter in such a way as to ensure that it is shorter than the length of the fastening section, or that the adapter exhibits different inner diameters.

In order to reversibly lock an adapter to the fastening section, the fastening section preferably comprises a seat in which a mounting unit formed on the adapter can be received. The mounting unit may, for example, take the form of a catch, which clicks into place in the seat. Thus, provision is made in particular for the seat to be formed on the free arm and/or on the arm connected to the base plate. Alternatively, the bar may comprise the seat. According to one preferred embodiment of the invention, one seat is located on the free arm as well as on the connecting arm. It is particularly preferable for the seat to be formed as an indentation, whereby the mounting unit takes the form of a bar corresponding to the indentation, which may be inserted into the indentation.

The base plate can have a recess between the pin and the tearing section, thus ensuring better hygiene. This reduces the contact points between the hand and/or the medical product/adhesive tape roll with the dispensing device, thus diminishing the risk of infection.

The base plate can have an edge at the end opposite the arm and for the recess to extend to the edge. This not only improves hygiene but also saves material and reduces weight.

To prevent the roll or the adhesive tape roll from sliding down, the pin can be fitted with a flange. This can be made of the same material as the pin, for example plastic, or an elastic material. Should the flange be of an elastic material in an alternate embodiment, it will be compressed when the (adhesive tape) roll slides over it. If the (adhesive tape) roll has been slid over the flange in its entirety, the flange decompresses, thereby fastening the (adhesive tape) roll to the pin. The diameter of the flange is selected to be larger than the inner diameter of the (adhesive tape) roll. Alternatively, or additionally, the adhesive tape roll may be clamped to the base plate by means of the elastic flange. In an alternate embodiment of the invention, the flange is only partly made of elastic material, wherein a preferred embodiment of the invention features an outer ring of the flange made of elastic material. In a further embodiment of the invention, the pin and flange may also be formed in two parts, so that the flange can be inserted on the pin. The roll or adhesive tape roll can be received on the pin by loosening the flange from the pin, attaching the roll, and then inserting the flange back on the pin.

To securely fasten the dispensing device to the rod, bar or the like, at least one fastening unit can be provided, for example, in the form of a screw, which is passed through an aperture formed in a first of the arms and which is screwed or bolted to a thread corresponding to the second arm. In an alternate embodiment, the fastening unit can be formed as a bolt, as a nut or as a locking bolt.

To secure the dispensing device along the rod, bar or the like, an aperture may further be formed in the second arm, through which a (threaded) section of the screw is passed, which is screwed with a nut.

The second arm can have an undercut on its side facing away from the first arm, designed to mount the nut essentially in a non-rotational manner relative to the second arm. The nut then serves as a counter nut for the bolt, whereby the undercut can also be designed such that the nut does not protrude beyond the surface of the connected arm. An easy to tighten or loosen manual mounting of the dispensing device to the rod, bar or the like, can be achieved by forming the at least one fastening unit as a wing screw.

The base plate may also feature a drill hole through which the base plate can be mounted to a wall, door or the like.

A stable dispensing device is thus provided, in particular, as characterized by the base plate and the fastening section, comprising the free arm, the crosspiece and the connected arm, being formed in one piece. Production processes such as injection molding or 3D printing may be considered.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
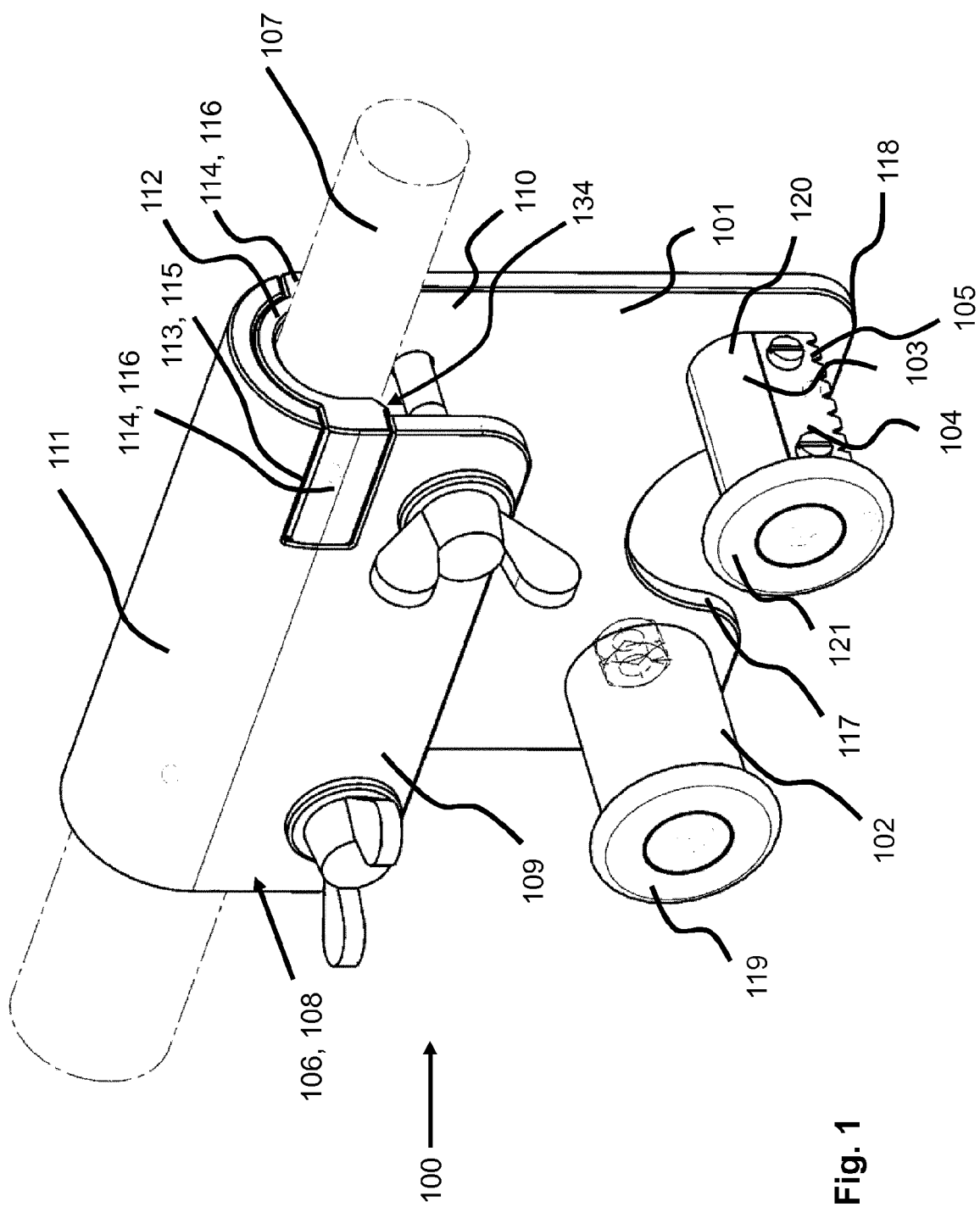
FIG. 1 is a perspective view of the dispensing device according to an exemplary embodiment of the present invention.

FIG. 1 shows a perspective view of the dispensing device 100 pursuant to the present invention for an adhesive tape roll, or for a medical product, such as a plaster, gauze bandage, bandaging material, etc., wound on a roll.

The dispensing device 100 has a base plate 101 equipped with a pin 102 for receiving the roll or the adhesive tape roll and a tearing section 103 having a tearing blade 104 at a distance from the pin 102. An adhesive tape roll, e.g. a roll of adhesive bandage, can be placed on the pin 102. In order to unwind the roll more easily, the pin 104 is formed rotationally symmetric along its longitudinal axis. The tearing blade 104 is equipped with teeth 105 to facilitate detaching of the adhesive tape or the medical product. The base plate 101 also comprises a fastening section 106 for partially gripping a rod 107. The fastening section 106 is formed as a clamping piece 108 for clamping the rod 107. It comprises a free arm 109 and an arm 110 connected to the base plate 101 and a crosspiece 111 connecting the free arm 109 to the arm 110. In the embodiment shown here, the crosspiece 111 is formed as an arc.

The dispenser 100 is characterized by providing at least one fastening unit 124 to join the connected arm 109, but in the present embodiment, in particular, by providing two of the fastening units 124 joining the free arm 109 to the connected arm 110 at the edges, and furthermore in that at least one fastening unit 124 joins the free arm 109 to the connected arm 110 in such a way as to form a receiving space 134 between the free arm 109, the crosspiece 111 and the connected arm 110 for receiving or for providing a passage for the rod 107 delimited by the at least one fastening unit 124.

The embodiment shown here contains an adapter 112 between the arm 110 and the free arm 109, the outer diameter of which is adapted to the inner diameter of the fastening section 106. The inner diameter of the adapter 112 can then be adapted to any diameter of the rod 107 being accommodated, preferably enhancing the clamping effect. The fastening section 106 features a seat 113 on the free arm 109 and on the arm 110 connected to the base plate 101, allowing for accommodation in each of a mounting unit 114 laterally attached to the adapter 112. This provides for a detachable connection between the adapter 112 and the fastening section 106. The seat 113 is formed as an indentation 115 and the mounting unit 114 as a bar 116 corresponding to the indentation 115. The bar 116 is adapted in such a way as to be inserted into the indentation 115.

Figure 3:
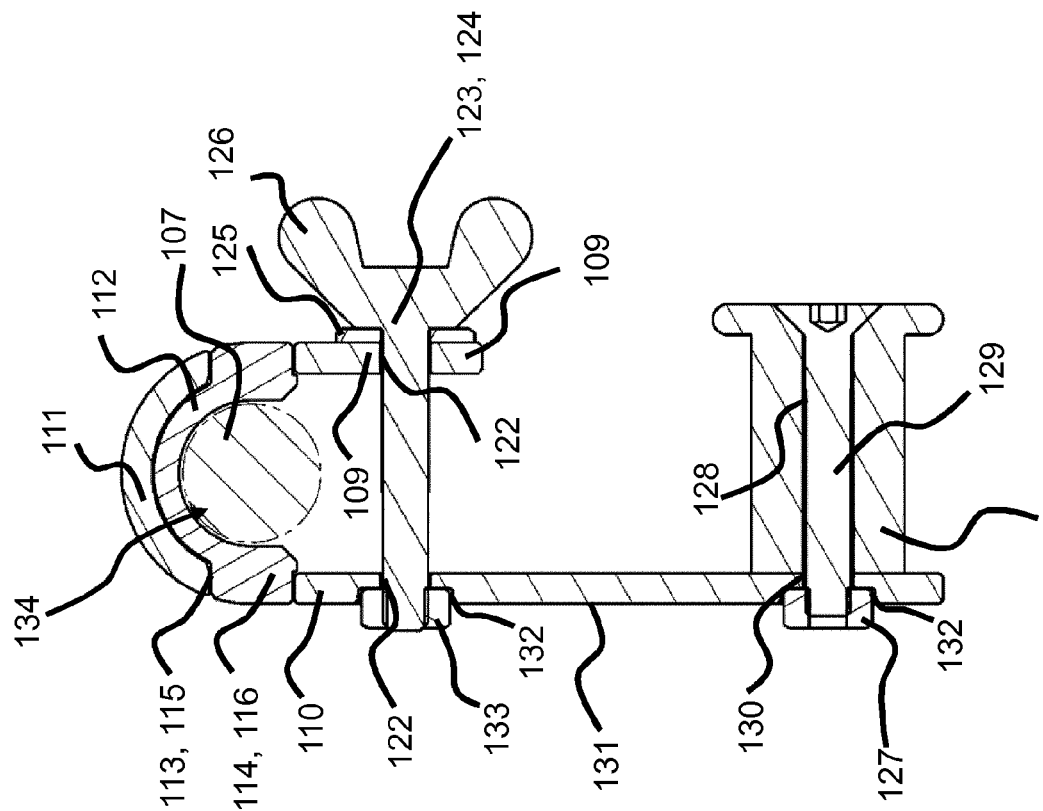
FIG. 3 illustrates the interface III-III from FIG. 2

The interaction between the indentation 115 and the bar 116 is further illustrated in FIG. 3. Preferably, the length of the adapter 112 is aligned with the width of the dispensing device 100. However, the length of the adapter may be less than 100 percent of the width of the dispensing device 100 spanning the bar 107, and preferably amounts at most to between 70 and 90 percent of the width of the dispensing device 100 and further preferably between 50 and 70 percent of the width of the dispensing device 100, or preferably between 20 and 50 percent of the width of the device 100. Thus, the device 100 may be attached to rods 107, which have different diameters throughout their length.

The base plate 101 has an indentation 117 between the pin 102 and the tearing section 103. The base plate 101 is provided with an edge 118 on its end situated opposite the arm 110 comprising the semicircular indentation 117. This minimizes the contact surface between the hands and the (adhesive tape) roll with the dispensing device 100, thus reducing the risk of infection.

Furthermore, the pin 102 is equipped with a flange 119, which secures the roll to be wound on the dispensing device 100. In one alternate embodiment of the invention, the flange 119 is made of an elastic material, enabling the (adhesive tape) roll to be compressed over the elastic flange 119 when it is fed on to the dispenser until it has reached its desired position on the pin 102. Upon inserting the roll, the flange 119 is compressed and decompressed again, when the roll is fed on to the pin 102. This prevents the (adhesive tape) roll from sliding off the pin 102 and facilitates handling.

The tearing section 103 is formed as a second pin 120 with a second flange 121, made of the same material as the first pin 102, preferably of plastic. The tearing blade 104 is attached to the tearing section 103 or to the other pin 120 with fastening elements, for example with two screws as shown here. This detachable attachment of the tearing blade 104 to the tearing section 103 facilitates replacement of the tearing blade 104 if it has become worn or blunt due to frequent use.

The dispensing device 100 is attached to the rod 107, firstly by means of the fastening section 106 gripping around it and secondly by means of an aperture 122 in the form of a drilled hole in the free arm 109 and in the arm 110 connected to the base plate 101, respectively. The aperture 122 comprises a fastening unit 124 formed of, for example, a wing screw 123.

Figure 2:
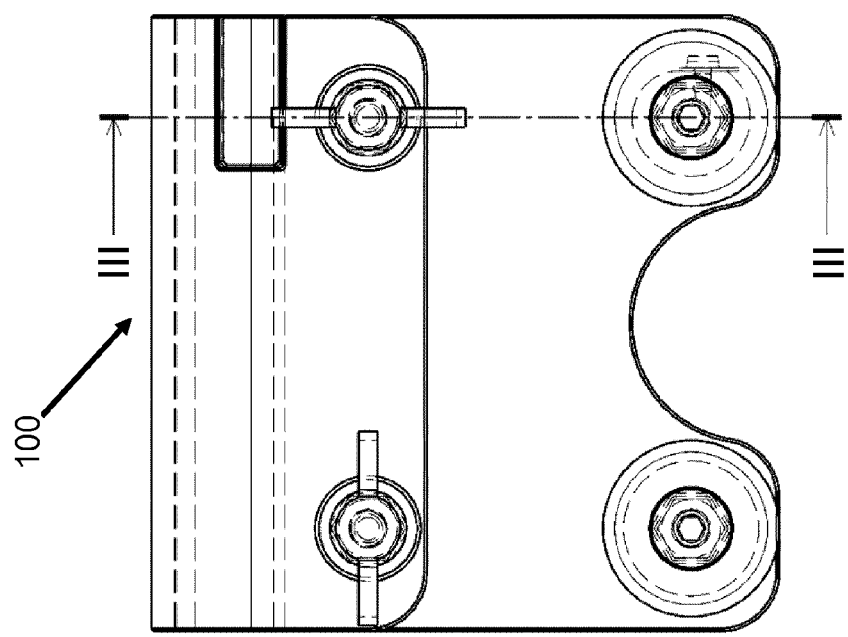
FIG. 2 depicts a frontal view of the dispensing device pursuant to the present invention.

FIG. 3 depicts the cross-section III-III from FIG. 2 of the dispensing device 100 pursuant to the present invention. In particular, the fastening mechanism of the dispensing device 100 to the rod 107 is illustrated. A washer 125 is disposed between the fastening unit 124 and the free arm 109. Moreover, the wing screw 123 is fitted with a nut 133 at the end opposite the wings 126, thus allowing the free arm 109 and the arm 110 connected to the base plate 101 to be positioned between the wings 126 of the wing screw 123 and the nut 133. By turning the wing screw 123, the rod 107 can be fixed or clamped in the fastening section 106, or it can be released. The wing screw 123 can consequently be screwed to the reverse 131 of the base plate 101 with a (counter) nut 133. To prevent the nut 133 from turning when the wing screw 123 is turned, it should be mounted non-rotatably. The embodiment shown here thus provides undercuts 132 on the reverse 131 approximately aligned to the dimensions of the nut 133. These undercuts 132 are formed in such a way as to prevent rotation or co-rotation of the nut 133. In order to clamp the rod 107, it is therefore sufficient to turn the wing screw 123, due to the self-locking position of the nut 133. This is advantageous particularly when the reverse 131 of the base plate 101 is not accessible for countering the nut 133 (manually).

Moreover, FIG. 3 depicts the mounting of the cylindrical second pin 120 or the tearing section 103 to the base plate 101. The tearing section 103 as well as the pin 102 not shown in FIG. 3 have an end-to end tunnel 128, in which a screw 129 or similar is accommodated. The base plate 101 has drill holes 130, allowing the tearing section 103 and the pin 102 to be mounted to the base plate 101 by means of the screw 130 and a nut 127. This also allows for the replacement of the pin 102 and/or the tearing section 103 in the event of damage or heavy usage. Again, the reverse 131 of the base plate 101 has undercuts 132, allowing insertion of the nuts 127 to counter the rotation of the screw 129.

Mounting the dispensing device 100 to the rod 107 by means of the fastening section 106 and the fastening units 124 allows for single-handed operation of the dispensing device 100. Contamination of the dispensing device 100, the roll or the adhesive roll is thus prevented as the hands only come into contact with the part of the adhesive tape roll or medical product that is wound on the roll which is torn off.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A device for dispensing an adhesive tape roll or for dispensing medical products stored on a roll, the device comprising:
   a base plate fitted with a pin upon which a roll or adhesive tape is adapted to be inserted;
   a tearing section with a tearing blade spaced at a distance from the pin;
   a fastening section connected to the base plate for at least partially encompassing a rod or a bar, the fastening section comprising a connected arm connected to the base plate, the connected arm merging with a crosspiece that is fixed to a free arm, such that the rod or the bar is accommodated between the free arm and the connected arm; and
   at least one fastening unit to join the connected arm to the free arm,
   wherein the base plate and the fastening section comprising the free arm, the crosspiece and the connected arm are formed as one piece, wherein the free arm and the connected arm allow for accommodation of an adapter between them, to adjust an inner diameter of the fastening section, and wherein the tearing section and the pin are both provided at a first end of the base plate which is opposite to a second end of the base plate having the fastening section.

2. The dispensing device according to claim 1, wherein the at least one fastening unit includes two fastening units that join the free arm with the connected arm at edges, respectively.

3. The dispensing device according to claim 1, wherein the at least one fastening unit joins the free arm to the connected arm in such a way as to form a receiving space between the free arm, the crosspiece and the connected arm for receiving or for providing a passage for the rod or the bar that is delimited by the at least one fastening unit.

4. The dispensing device according to claim 1, wherein the at least one fastening unit joins the free arm to the connected arm in such a way as to clamp the rod or the bar received in the fastening section.

5. The dispensing device according to claim 1, wherein the at least one fastening unit is provided in the form of a screw, which is passed through an aperture formed in a first one of the free arm or the connecting arm and which is screwed or bolted to a second one of the free arm or the connecting arm.

6. The dispensing device according to claim 5, wherein the second one of the free arm or the connecting arm also comprises an aperture, through which a section of the screw is passed and which is screwed with a nut.

7. The dispensing device according to claim 6, wherein the second one of the free arm or the connecting arm comprises an undercut on a side facing away from the first one of the free arm or the connecting arm, which is designed to mount the nut essentially in a non-rotational manner relative to the second one of the free arm or the connecting arm.

8. The dispensing device according to claim 1, wherein the at least one fastening unit is formed as a wing screw.

9. The dispensing device according to claim 1, wherein the adapter extends throughout an entire length of the fastening section.

10. The dispensing device according to claim 1, wherein the fastening section comprises a seat allowing for accommodation of a mounting unit attached to the adapter and thus facilitating a detachable connection between the adapter and the fastening section.

11. The dispensing device according to claim 1, wherein the base plate comprises an indentation between the pin and the tearing section.

12. The dispensing device according to claim 11, wherein the base plate comprises an edge at the first end thereof and wherein the indentation extends to the edge.

13. The dispensing device according to claim 1, wherein the pin comprises a flange made of an elastic material.

14. The dispensing device according to claim 1, wherein the at least one fastening unit includes a screw, and wherein a longitudinal axis of the screw extends perpendicular to a longitudinal axis of the rod or the bar.

15. The dispensing device according to claim 14, wherein the rod or the bar is cylindrical shaped.

16. The dispensing device according to claim 1, wherein the rod or the bar is cylindrical shaped.

17. The dispensing device according to claim 1, wherein the crosspiece is arc shaped.

18. The dispensing device according to claim 1, wherein the at least one fastening unit directly contacts both the connected arm and the free arm.

* * * * *